United States Patent [19]
Stine et al.

[11] Patent Number: 6,027,514
[45] Date of Patent: Feb. 22, 2000

[54] APPARATUS AND METHOD FOR REMOVING OCCLUDING MATERIAL FROM BODY LUMENS

[75] Inventors: John G. Stine, San Jose; David W. Snow; John B. Simpson, both of Woodside; Martin F. Overbeek Bloem, San Bruno, all of Calif.

[73] Assignee: Fox Hollow Technologies, Inc., Menlo Park, Calif.

[21] Appl. No.: 08/982,231

[22] Filed: Dec. 17, 1997

[51] Int. Cl.[7] ................................................. A61B 17/22
[52] U.S. Cl. ........................... 606/159; 600/564; 606/167; 606/174
[58] Field of Search ..................... 600/562–568; 604/19, 22; 606/1, 127, 159, 167, 170, 171, 174, 184, 185, 180

[56] References Cited

U.S. PATENT DOCUMENTS

| | | | |
|---|---|---|---|
| Re. 33,258 | 7/1990 | Onik et al. ................................ | 604/22 |
| 2,178,790 | 11/1939 | Henry . | |
| 3,705,577 | 12/1972 | Sierra . | |
| 3,815,604 | 6/1974 | O'Malley et al. . | |
| 3,837,345 | 9/1974 | Matar ....................................... | 606/159 |
| 3,995,619 | 12/1976 | Glatzer . | |
| 4,210,146 | 7/1980 | Banko . | |
| 4,696,298 | 9/1987 | Higgins et al. . | |
| 4,819,635 | 4/1989 | Shapiro . | |
| 4,994,067 | 2/1991 | Summers ................................. | 606/159 |
| 5,087,265 | 2/1992 | Summers ................................. | 606/159 |
| 5,226,910 | 7/1993 | Kajiyama et al. ....................... | 606/171 |
| 5,242,460 | 9/1993 | Klein et al. .............................. | 606/159 |
| 5,250,065 | 10/1993 | Clement et al. ......................... | 606/172 |
| 5,285,795 | 2/1994 | Ryan et al. . | |
| 5,312,425 | 5/1994 | Evans et al. ............................. | 606/155 |
| 5,395,313 | 3/1995 | Naves et al. ............................. | 604/22 |
| 5,431,673 | 7/1995 | Summers et al. ....................... | 606/170 |
| 5,505,210 | 4/1996 | Clement . | |
| 5,571,130 | 11/1996 | Simpson et al. ........................ | 606/171 |
| 5,584,842 | 12/1996 | Fogarty et al. .......................... | 606/159 |
| 5,674,232 | 10/1997 | Halliburton ............................. | 606/159 |
| 5,709,698 | 1/1998 | Adams et al. ........................... | 606/180 |

*Primary Examiner*—Glenn K. Dawson
*Attorney, Agent, or Firm*—Townsend and Townsend and Crew LLP

[57] ABSTRACT

An atherectomy catheter includes a catheter body having a blade assembly at its distal end. The blade assembly includes first blade and a second blade, where each blade has an opposed cutting edge. At least one of the cutting edges will have a penetrating point formed thereon. Preferably, both edges will have at least one aligned cutting point, more preferably at least two or more aligned cutting points. When the blades are actuated to shear tissue therebetween, the cutting points act to penetrate and capture the material to be sheared.

66 Claims, 16 Drawing Sheets

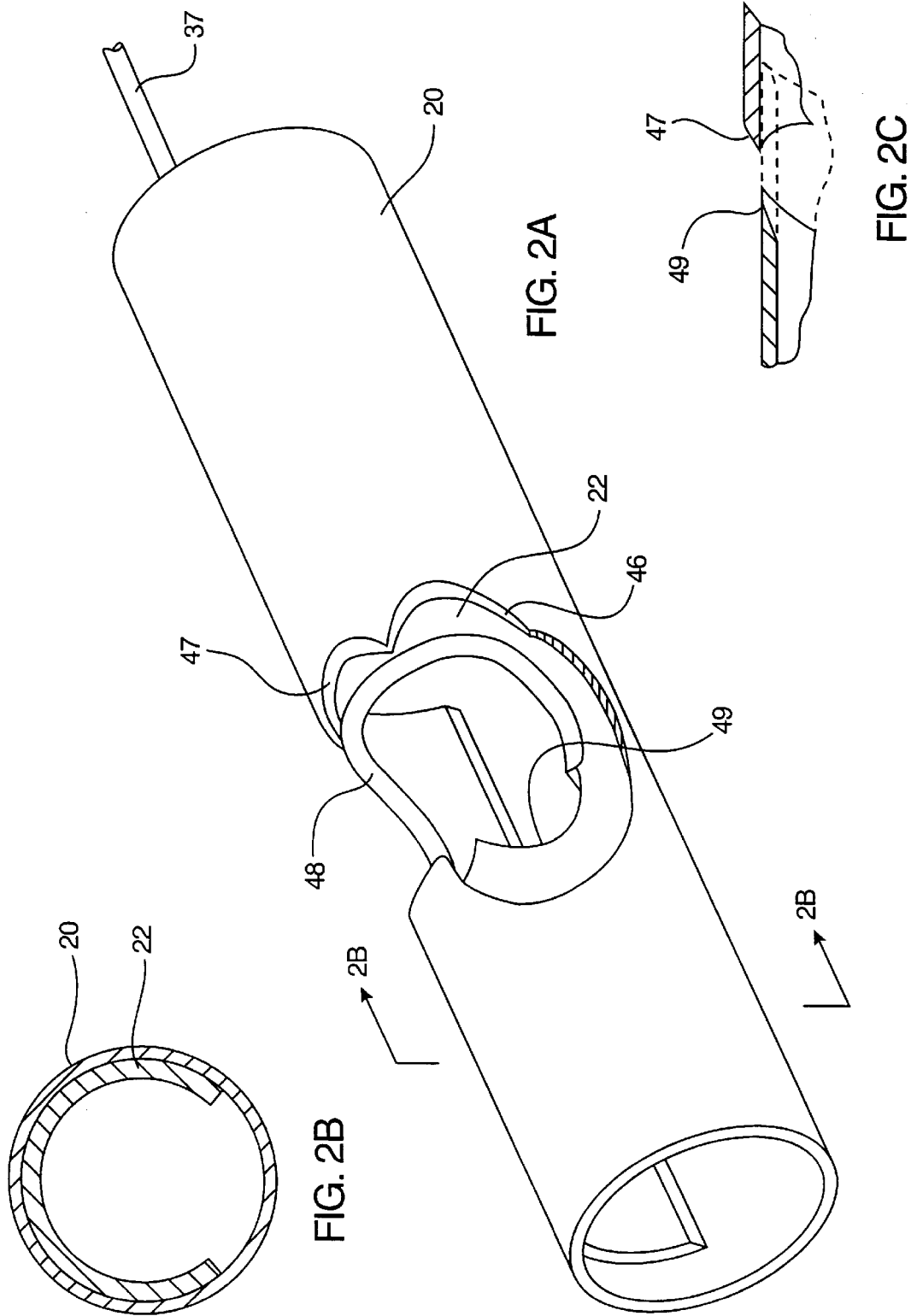

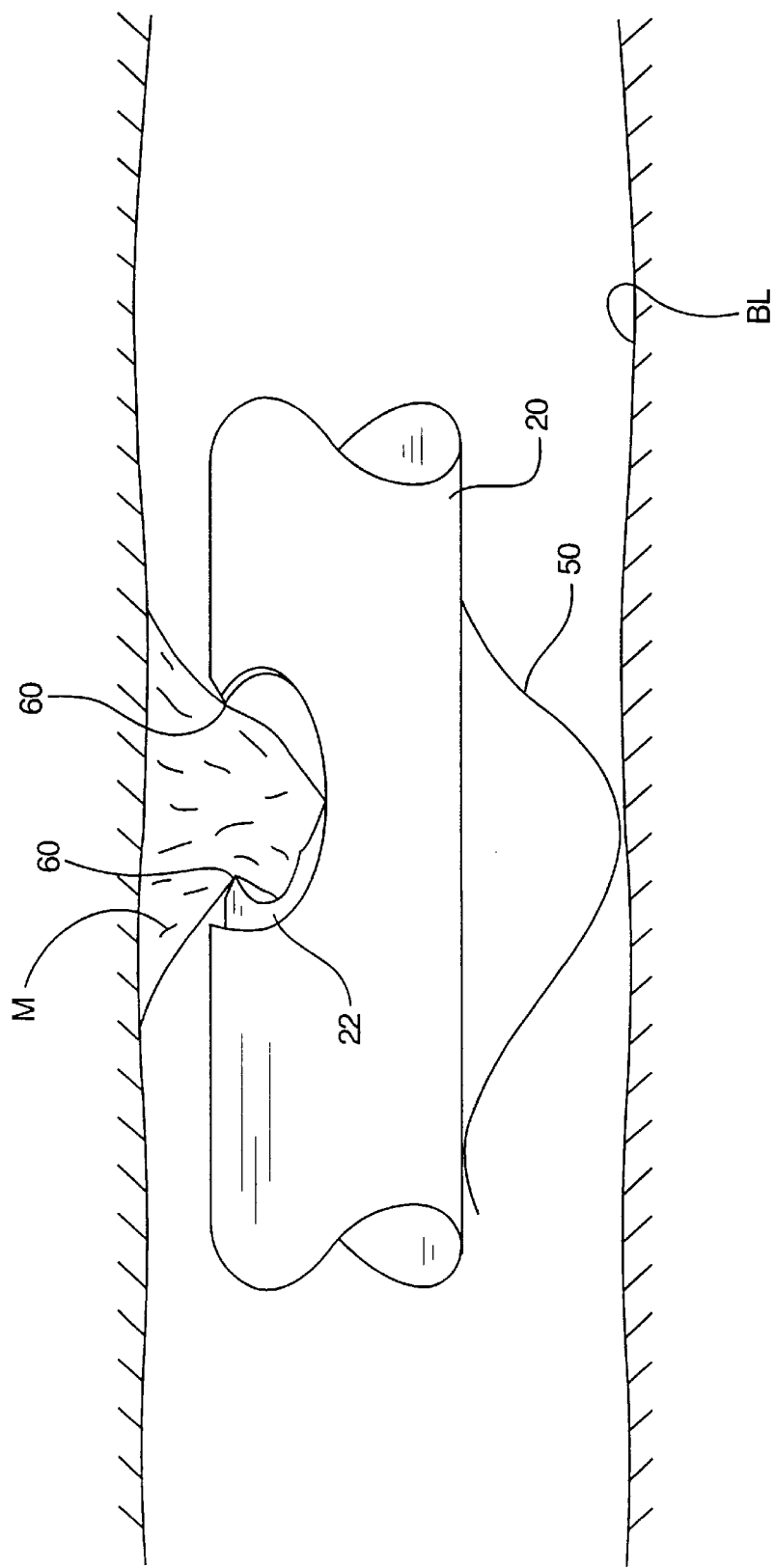

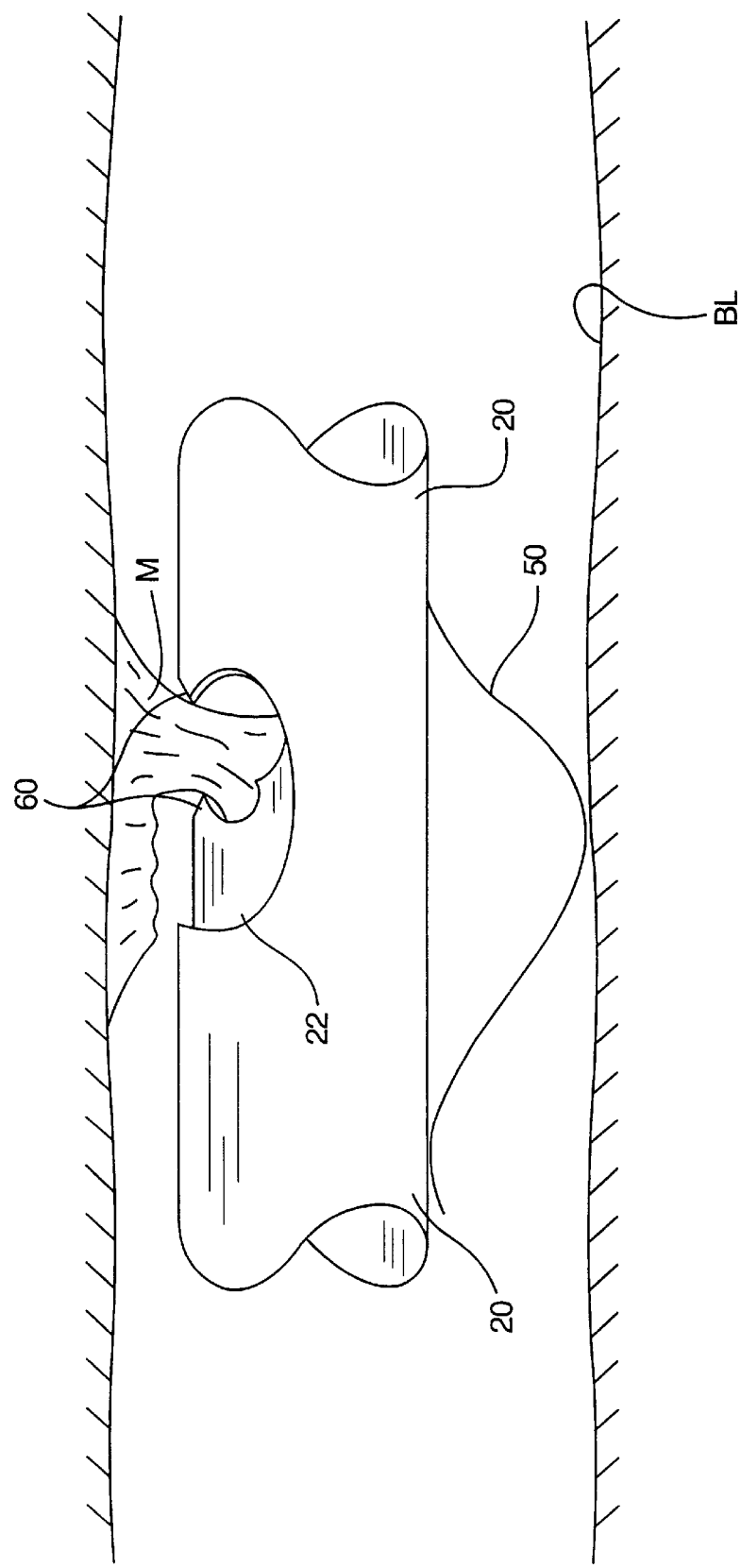

APPARATUS AND METHOD FOR REMOVING OCCLUDING MATERIAL FROM BODY LUMENS

BACKGROUND OF THE INVENTION

1. Field of the Invention

The present invention relates generally to apparatus and methods for removing occluding materials from body lumens. More particularly, the present invention relates to the construction and use of atherectomy catheters for excising atheroma and other materials from blood vessels.

Cardiovascular disease frequently arises from the accumulation of atheromatous material on the inner walls of vascular lumens, particularly arterial lumens of the coronary and other vasculature, resulting in a condition known as atherosclerosis. Atherosclerosis occurs naturally as a result of aging, but may also be aggravated by factors such as diet, hypertension, heredity, vascular injury, and the like. Atheromatous and other vascular deposits restrict blood flow and can cause ischemia which, in acute cases, can result in myocardial infarction. Atheromatous deposits can have widely varying properties, with some deposits being relatively soft and others being fibrous and/or calcified. In the latter case, the deposits are frequently referred to as plaque.

Atherosclerosis can be treated in a variety of ways, including drugs, bypass surgery, and a variety of catheter-based approaches which rely on intravascular widening or removal of the atheromatous or other material occluding a blood vessel. Of particular interest to the present invention, a variety of methods for cutting or dislodging material and removing such material from the blood vessel have been proposed, generally being referred to as atherectomy procedures. Atherectomy catheters intended to excise material from the blood vessel lumen generally employ a rotatable and/or axially translatable cutting blade which can be advanced into or past the occlusive material in order to cut and separate such material from the blood vessel lumen. In particular, side-cutting atherectomy catheters generally employ a housing having an aperture on one side, a blade which is rotated or translated by the aperture, and a balloon or other deflecting structure to urge the aperture against the material to be removed.

Although atherectomy catheters have proven to be very successful in treating many types of atherosclerosis, some catheter designs suffer from certain limitations. For example, many side-cutting atherectomy catheters have difficulty in capturing occluding material in the cutting aperture. To facilitate material capture, the cutting aperture is frequently elongated to increase the area into which the material can penetrate. While such elongation is effective, it requires an equivalent lengthening of the cutter housing. Most cutter housings are rigid, and such lengthening makes it more difficult to introduce the distal end of the catheter through torturous regions of the vasculature. Moreover, having a cutting blade travel over a lengthy cutter aperture increases the risk of penetrating the vascular wall.

For these reasons, it is desired to provide atherectomy catheters which can access even small, tortuous regions of the vasculature and which can remove atheromatous and other occluding materials from within blood vessels in a controlled fashion with minimum risk of injuring the blood vessel wall. In particular, it is desired to provide atherectomy catheters which can facilitate capturing and invaginating atheromatous materials with relatively short cutter mechanisms. The catheters and methods for use in a variety of body lumens, including but not limited to coronary and other arteries. At least some of these objectives will be met by the catheter and method of the present invention described hereinafter and in the claims.

2. Description of the Background Art

Atherectomy catheters having axially reciprocatable, non-rotating blades are described in U.S. Pat. Nos. 5,674,232 and 4,994,067. Other atherectomy catheters are described in U.S. Pat. Nos. 5,571,130; 5,431,673; 5,312,425; 5,242,460; and 5,087,265. A household knife having a V-shaped cutting edge is described in U.S. Pat. No. 2,178,790. Surgical cutters and biopsy devices having axially translatable and/or rotatable cutting blades are described in U.S. Pat. Nos. 5,505,210; 5,395,313; 5,285,795; 5,226,910; 5,250,065; 3,815,004; 4,819,635; 4,696,298; 4,210,146; 3,995,619; 3,705,577; and Re. 33,258.

SUMMARY OF THE INVENTION

According to the present invention, a catheter for removing occluding and other materials from a body lumen, particularly for removing atheromatous material from a blood vessel, comprises a catheter body having a proximal end and a distal end. First and second blades having cutting edges are disposed near the distal end of the catheter body, and an actuator is operatively linked to the blades to draw their respective cutting edges together to capture and shear material located between the blades. In order to facilitate capture of the material, at least one of the blades will have a cutting point disposed along its cutting edge in order to penetrate and engage material disposed between the blades. In particular, as the cutting blade having the penetrating point is advanced, the point will penetrate into the material and prevent the material from being pushed away from the blade.

Preferably, the cutting edges of both the first and second blades will have such penetrating points. More preferably, at least one of the penetrating points on the first cutting blade will be aligned with one of the penetrating points on the second cutting blade so that they meet as the blades are drawn together. By providing the blades with edges which recede from the penetrating points, preferably along arcuate lines, the cutting edges of the blades will provide an angled shearing motion which has been found to be very effective in capturing and shearing atheromatous and other occluding materials which are initially captured by the penetrating points. In particularly preferred embodiments, the cutting blades will each have at least two penetrating points aligned with each other, and even more preferably have at least three penetrating points aligned with each other.

The cutting edges may be drawn together in either an axial or circumferential direction. Usually, the cutting edges will not rotate or otherwise be moved with respect to each other, other than in the direction in which they are drawn together. In some instances, however, it may be desirable to oscillate the blades relative to each other in order to further enhance the shearing action. Such oscillation, however, may decrease the ability of the penetrating points to capture and maintain the occluding material between the blades.

In a first exemplary embodiment, the cutting blades are drawn together in an axial direction (as defined with respect to the catheter body) by an actuator comprising a rod having a distal end attached to one of the blades and a proximal end having a slider for manual advancement, typically being disposed within a proximal hub or handle. Preferably, the rod will be radially offset within the catheter body and axially aligned with the cutting edge on the cutting blade. Such alignment transmits the cutting motion to the cutting edge of the blade in a direct, efficient manner.

In another aspect of the catheter, the first blade is fixedly attached to the distal end of the catheter body and the second blade is disposed to move within the first blade in order to pass the cutting edges by each other. In a specific embodiment, the first and second blades are arranged as coaxial tubes with side apertures which define the cutting edges. The cutting edges may be disposed transversely so that the cutting edges are axially opposed, in which case the actuator will translate the second blade axially relative to the first blade. Alternatively, the cutting edges may be disposed axially, in which case the actuator rotates the second blade relative to the first blade to draw the cutting blade together circumferentially. In either case, the inner blade may be spring-biased so that its cutting edge is aligned to shear closely against the cutting edge of the first blade. For example, the inner blade may be in the form of a split tube which is biased so that its outer surface engages an inner surface with the outer tubular blade.

The catheters of the present invention will optionally further include a mechanism for urging the distal end of the catheter body in a transverse direction when the catheter body is in a body lumen, e.g. a blood vessel. For example, the urging mechanism may comprise a resilient ski that projects radially outwardly from the catheter body, typically on the side of the catheter body opposite to the cutting mechanism. In the exemplary embodiment, the resilient ski is fully extended in the radial position in the absence of a constraining force, e.g., a guiding catheter or body lumen. In alternative embodiments, the resilient ski or other deflecting mechanism may be selectively actuated, e.g., using a radially extensible element and an axially translatable element which cooperate to extend the ski or other member radially outward. The urging mechanism could also comprise a balloon structure, although that is not presently preferred.

A preferred atherectomy catheter according to the present invention comprises a catheter body having a proximal end, a distal end, and a lumen therethrough. A first tubular blade having an interior is attached to the distal end of the catheter body so that its interior opens into the lumen of the catheter body. A second tubular blade is coaxially disposed within the interior of the first tubular blade. The blades each have side apertures defining transverse, opposed cutting edges, and each of the cutting edges has at least one penetrating point aligned with the penetrating point on the other cutting edge. An actuator is disposed at the proximal end of the catheter body and operatively connected to axially translate the second tubular blade relative to the first tubular blade to cause the penetrating points to penetrate material within the apertures and thereafter to cause the cutting edges to shear material within the apertures. The actuator typically comprises a rod, as described above, and the blades preferably include at least two aligned penetrating points, and more preferably at least three aligned penetrating points. The inner tubular blade is preferably radially spring-biased within the first tubular blade, as described above, and an urging mechanism may be provided on the outer tubular blade, also as discussed above.

The present invention still further provides methods for excising occlusive material from body lumens, particularly atheroma, thrombus, or plaque from within blood vessels, including the coronary arteries and peripheral vasculature. The method comprises disposing first and second blades within body lumen so that a cutting edge on each blade is on one side on the portion of the material to be removed. At least one of the cutting blades has a penetrating point on its cutting edge, preferably multiple cutting points as discussed above. The blades are then drawn together so that the penetrating point(s) penetrate into and capture said material. The blades are further drawn together to shear the portion with the cutting edges.

In specific aspects of the method, the cutting blades are typically disposed within the body lumen by advancing a catheter intraluminally within the body lumen. The drawing/excising step will typically remove relatively small amounts of material, usually in the range from 0.1 mg to 5 mg, preferably in the range from 1 mg to 2 mg. Thus, the method of the present invention may be repeated multiple times, typically from 10 times to 100 times, more typically from 25 times to 75 times, often from 40 to 60 times, in order to remove an occluding amount of atheromatous material from a blood vessel.

As discussed above in connection with the apparatus, the blades may be axially translated relative to each other or may be rotated in a circumferential direction relative to each other. The excised material may be captured within the catheter body and either extracted from the catheter body while the catheter remains in situ or retained within the catheter body and removed together with removal of the entire catheter. Although the provision of penetrating points greatly facilitates the capture and invagination of material to be removed into the cutting mechanism, the method may further comprise urging the cutting side of the catheter body against the material to be removed, typically using resilient skis as described above.

BRIEF DESCRIPTION OF THE DRAWINGS

FIG. 2A is an enlarged view of the cutter blades of FIG. 2 with portions broken away.

FIG. 2B is a cross-section taken along line 2B—2B of FIG. 2A.

FIG. 2C is an enlarged detail view illustrating how the honed edges of the cutting blades at the catheter of FIG. 2A meet.

FIGS. 4A–4D illustrate use of the atherectomy catheter of FIGS. 1 and 2 for removing a portion of an occluding mass within a body lumen according to the method of the present invention.

DESCRIPTION OF THE SPECIFIC EMBODIMENTS

Figure 1:
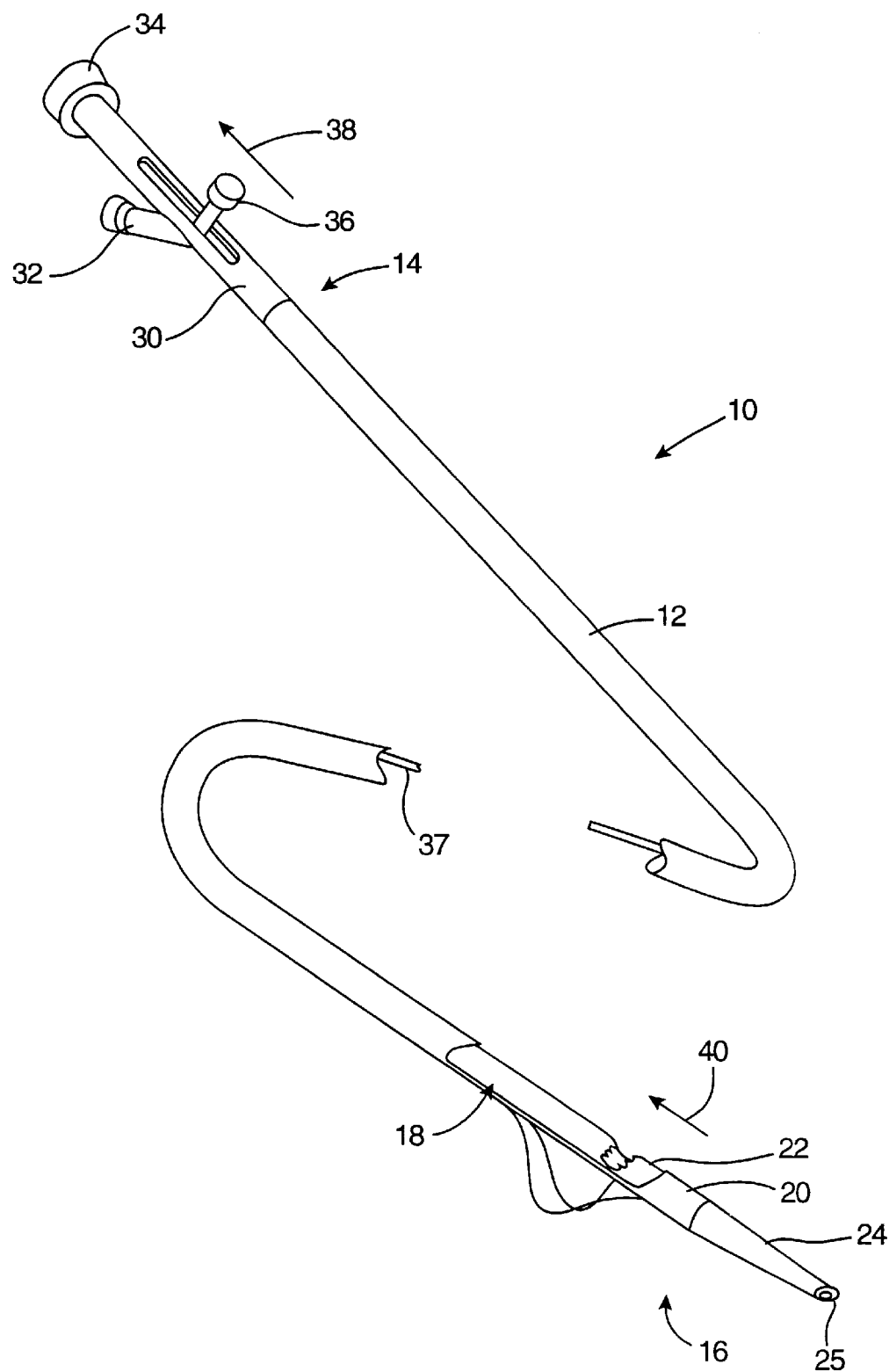
FIG. 1 is a perspective view of an atherectomy catheter constructed in accordance with the principles of the present invention.

Apparatus and methods according to the present invention will generally be adapted for the intraluminal treatment of a target site within a body lumen of a patient, usually in a coronary artery or peripheral blood vessel which is occluded with atherosclerotic or other material. The apparatus and methods, however, are also suitable for treating other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

Apparatus according to the present invention will comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the catheter bodies will typically be very flexible and suitable for introduction over a guidewire to a target site within the vasculature. In particular, catheters can be intended for "over-the-wire" introduction when a guidewire lumen extends fully through the catheter body or for "rapid exchange" introduction where the guidewire lumen extends only through a distal portion of the catheter body. Catheter bodies intended for intravascular introduction will typically have a length in the range from 50 cm to 200 cm and an outer diameter in the range from 1 French (0.33 mm; Fr.) to 12 Fr., usually from 3 Fr. to 9 Fr. In the case of coronary catheters, the length is typically in the range from 125 to 200 cm, the diameter is preferably below 8 Fr., more preferably below 7 Fr., and most preferably in the range from 2 Fr. to 7 Fr. Catheter bodies will typically be composed of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, axial filaments, or the like, in order to increase rotational strength, column strength, toughness, pushability, and the like. Suitable catheter bodies may be formed by extrusion, with one or more lumens being provided when desired. The catheter diameter can be modified by heat expansion and shrinkage using conventional techniques. The resulting catheters will thus be suitable for introduction to the vascular system, often the coronary arteries, by conventional techniques.

First and second cutting blades will be disposed at or near the distal end of the catheter body and will have cutting edges, typically oriented in an opposed manner. The cutting blades will usually be formed from a metal, but could also be formed from hard plastics, ceramics, or composites of two or more materials, which can be honed or otherwise formed into the desired cutting edge. In the exemplary embodiments, the cutting blades are formed as coaxial tubular blades with the cutting edges defined in aligned apertures therein. It will be appreciated that the present invention is not limited to such preferred cutting blade assemblies, in a variety of other designs, such as the use of wiper blades, scissor blades or the like. Optionally, the cutting edge of either or both the blades may be hardened, e.g. by chrome plating. A preferred chrome plating material is ME-92, available from ME-92 Operations, Inc., which may be applied according to manufacturer's instructions.

Figure 2:
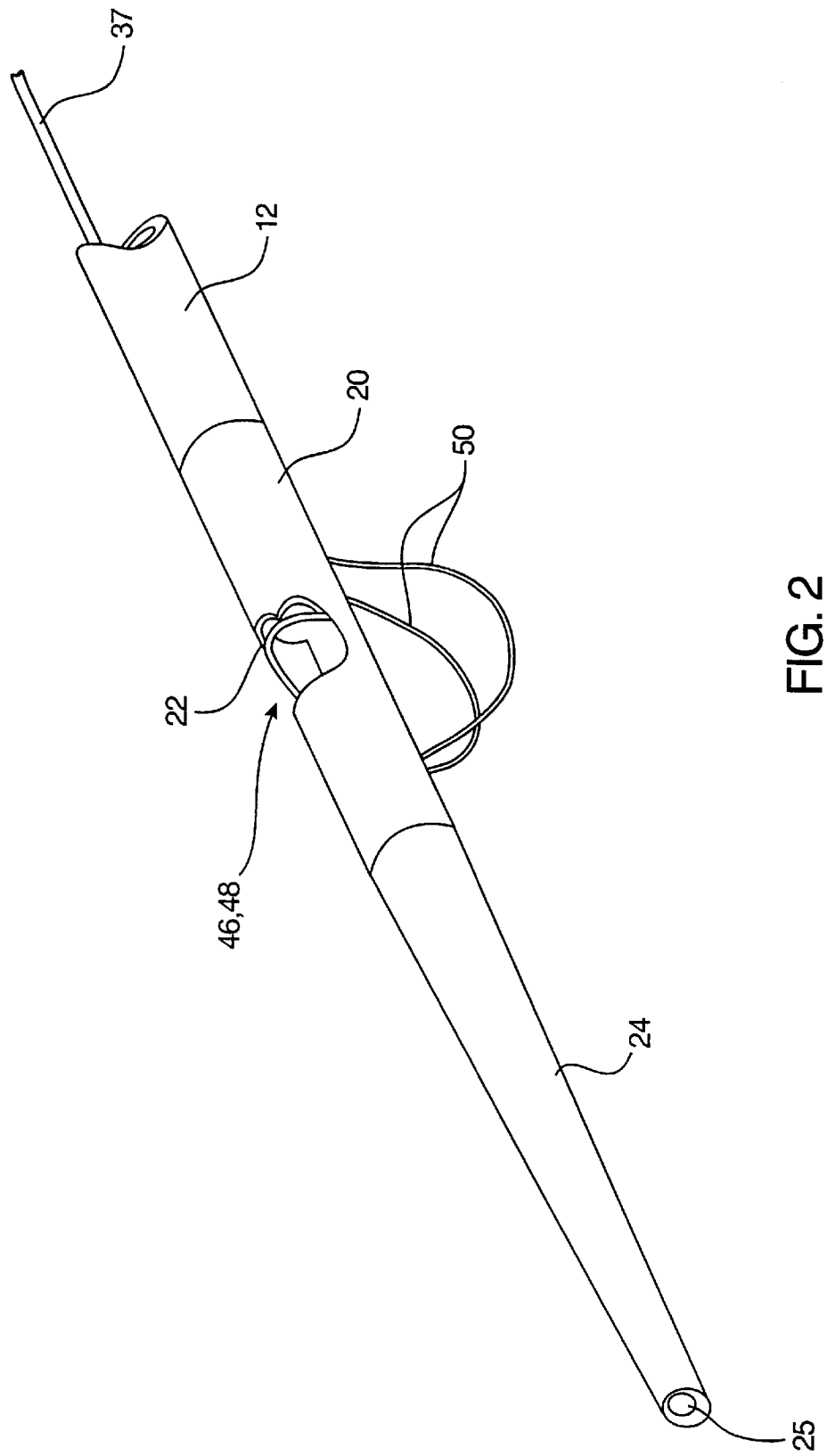
FIG. 2 is a detailed view of the distal end of the atherectomy catheter of FIG. 1.

Referring now to FIGS. 1 and 2, a catheter 10 constructed in accordance with the principles of the present invention comprises a catheter body 12 having a proximal end 14 and a distal end 16. A cutting mechanism 18 comprising an outer blade 20 and an inner blade 22 is attached to the distal end of the catheter body 12. An atraumatic tip 24 is attached to the distal end of the outer cutting blade 20, and a guidewire lumen 25 extends through the entire catheter body, cutting mechanism 18, and terminates in port 25 at the distal tip of tip section 24. A proximal hub 30 is attached to the proximal end of catheter body 12 and comprises a perfusion/aspiration connector 32, a guidewire connector 34, and a slider 36. The slider 36 is attached to the proximal end of an actuator rod 37 which extends from the hub 30 through the lumen of catheter body 12 into the cutting mechanism 18 where it is attached at a proximal end of the inner cutting blade 22. In this way, manual actuation of slider 36 in the direction of arrow 38 moves inner cutting blade 22 in the direction of arrow 40.

The outer cutting blade 20 has an aperture 46 formed in one side thereof, as best seen in FIG. 2A. A cutting edge 47 is formed into a transverse peripheral portion of the aperture 46 and includes a plurality of penetrating points as will be described in more detail hereinafter. A second aperture 48 is formed in the side of the inner cutting blade 22, where aperture 48 includes a cutting edge formed in a transverse peripheral region thereof which is opposed to the cutting edge 47 of aperture 46. In this way, the cutting edges 47 and 49 of apertures 46 and 48 and blades 20 and 22 will be drawn past each other when the slider 36 (FIG. 1) is drawn in the proximal direction of arrow 38 to translate rod 37. In a preferred aspect of the present invention, the inner cutting blade 22 is an axially split tubular member which is sized (in its unbiased state) to have an outer diameter slightly larger than the inner diameter of tubular cutting blade 20 (FIG. 2B). Thus, when the inner blade 22 is disposed within the interior of outer blade 20, the outer surface of blade 22 will be slightly constrained and have its outer surface spring-biased against the inner surface of blade 20. In this way, close contact between the blades is assured and shearing between the cutting edges 47 and 49 is enhanced.

The cutting mechanism at the distal end of catheter 10 will include a further mechanism for urging it in a radial direction aligned with the apertures 46 and 48. In particular, a pair of resilient ski members 50 may be provided on the side of the outer blade 20 which is opposite to that of the apertures 46 and 47. As described in more detail later in connection with FIGS. 5A–5C, the mechanism 50 may be passive or active.

Figure 3A:
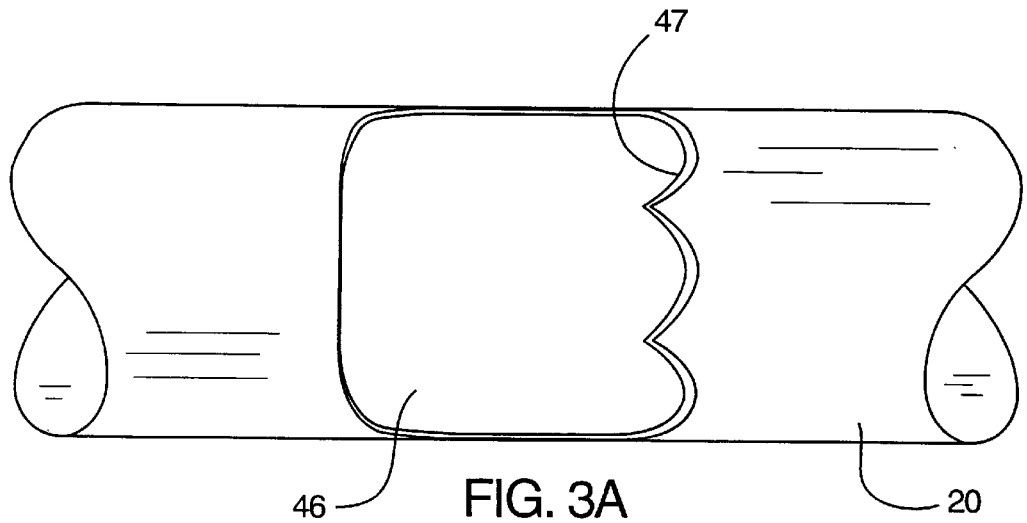
FIGS. 3A–3E are top and detail views of the cutting mechanism of the atherectomy catheter of FIGS. 1 and 2 illustrating axial translation of a second, inner cutting blade relative to a first, outer cutting blade.
Figure 3B:
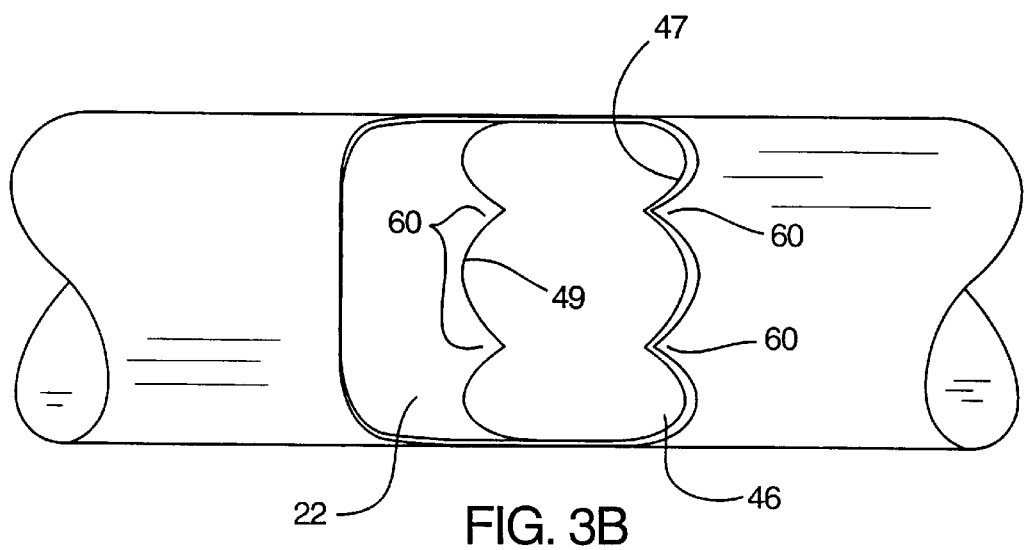
Figure 3C:
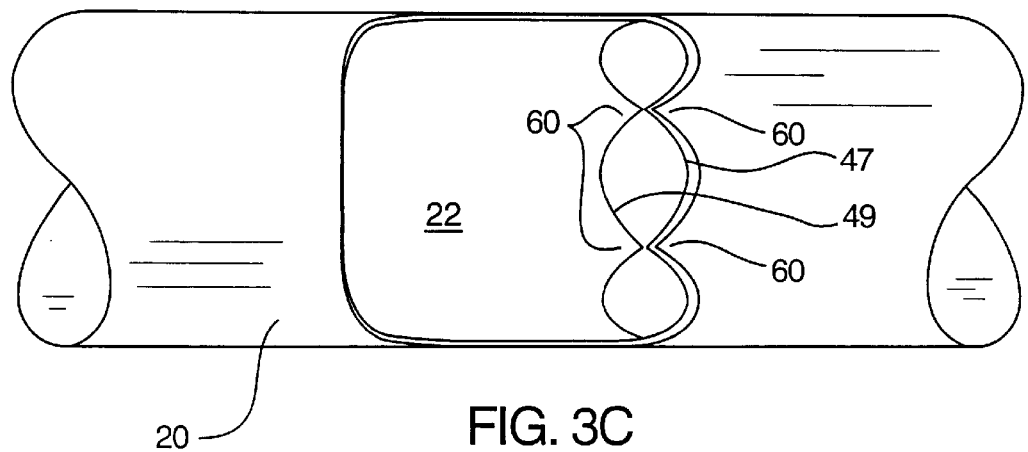
Figure 3D:
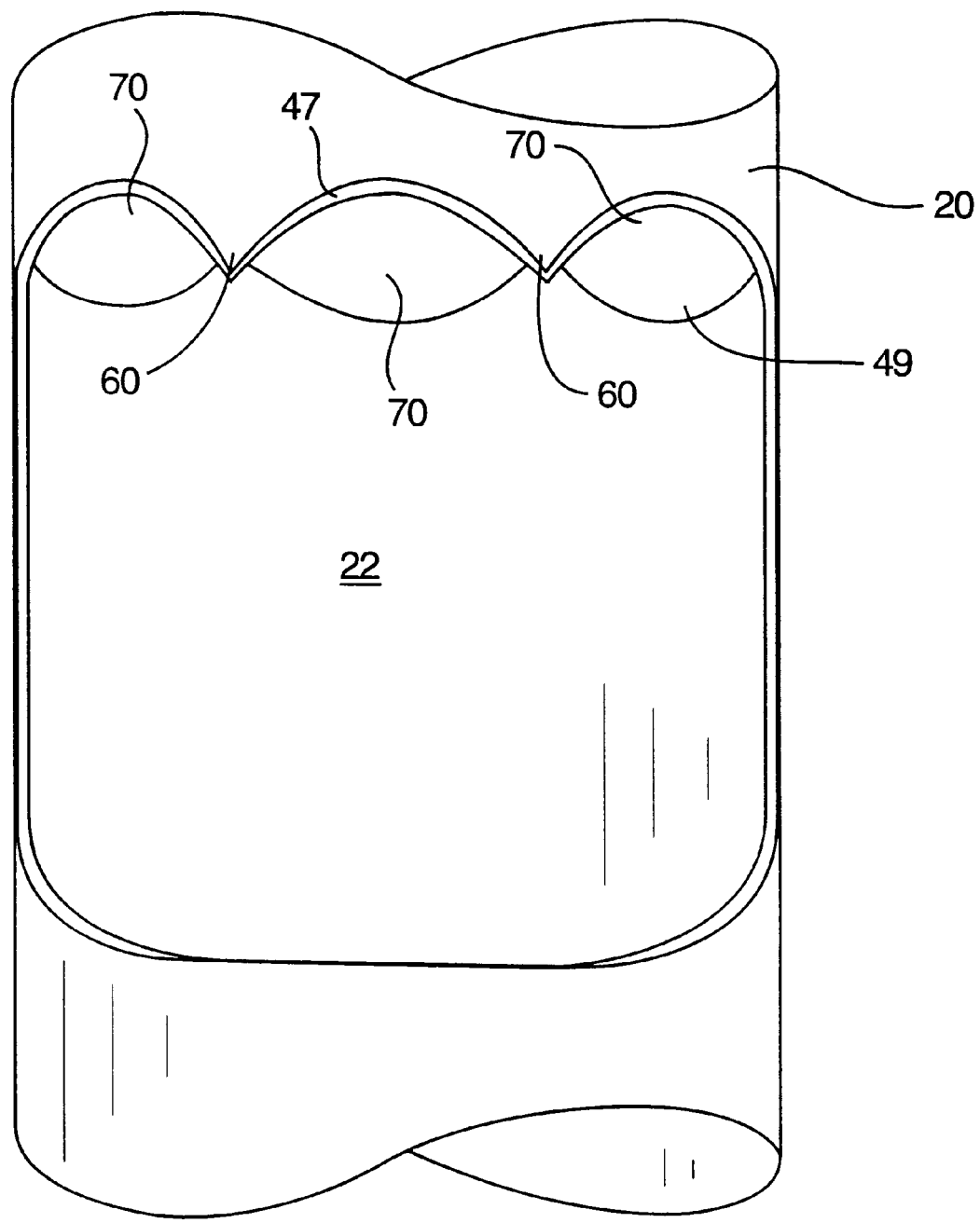
Figure 3E:
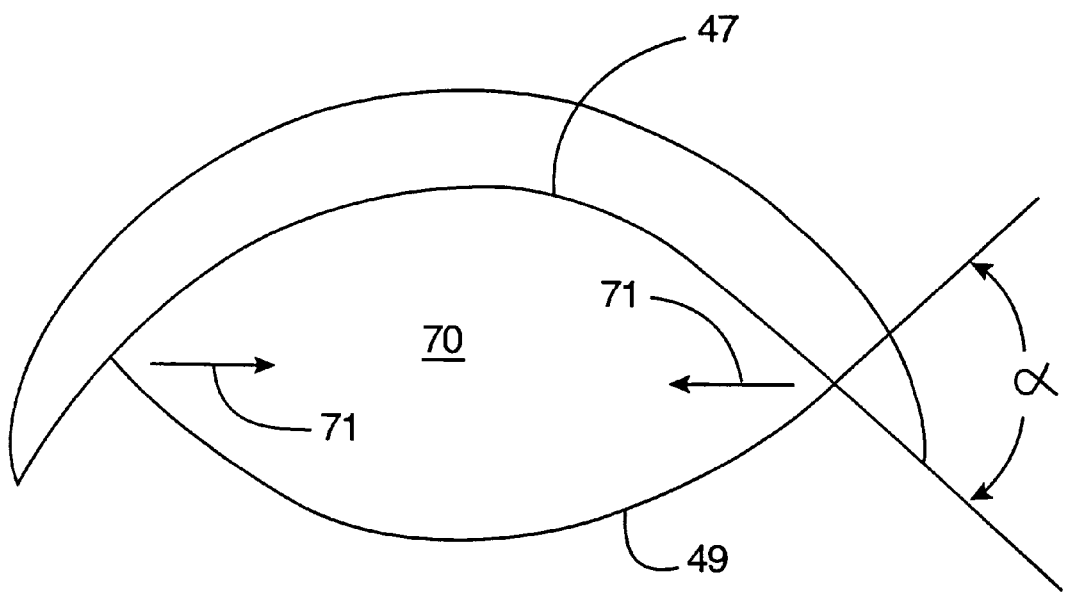

Referring now to FIGS. 3A–3E, actuation of the 47 and 49 of blades 20 and 22 will be described in more detail. Initially, before a cut is commenced, the inner blade 20 will usually be distally retracted so that cutting edge 49 lies outside of the aperture 46, as illustrated in FIG. 3A. The cutting edges 47 and 49 are preferably honed (i.e., sharpened or otherwise formed to sharp cutting edges) with one flat surface and one chamfered surface. The blades are disposed so that the flat surfaces of the cutting edges 47 and 49 slide past each other as the blades are actuated, as illustrated in FIG. 2C. The inner cutting blade 22 is then advanced proximally using rod 37 so that cutting edge 49 enters into the aperture 46, as illustrated in FIG. 3B. Each of the cutting edges 47 and 49 includes penetrating points 60 which are axially aligned so that they will meet when the inner cutting blade 22 is sufficiently retracted in the distal direction, as shown in FIG. 3C. After initially meeting, as shown in FIG. 3C, penetrating points 60 and remainder of the cutting edges 47 and 49 will pass each other in a shearing action, as shown in FIG. 3D. The cutting edges 47 and 49 and penetrating points 60 thus define a plurality of peripherally constrained excision regions 70, where material to be removed is trapped and efficiently excised from the luminal wall. As illustrated in FIG. 3E, the arcuate cutting edges between adjacent penetrating points 60 meet at an angle α which varies as the blades pass each other.

Figure 3F:
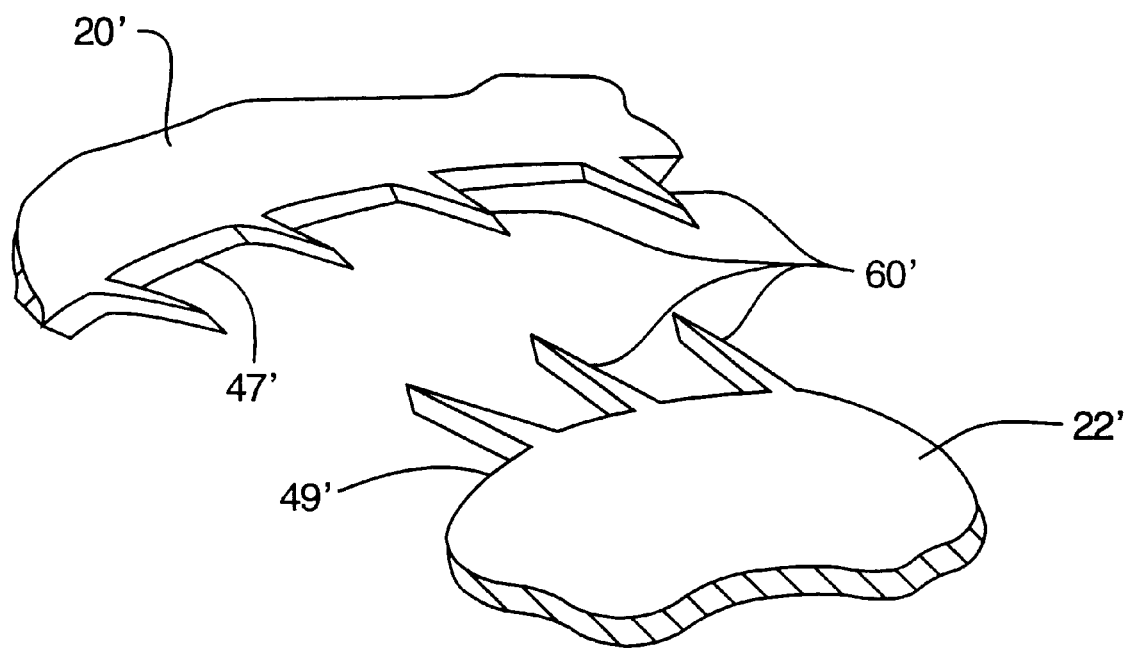
FIG. 3F is an alternative configuration of a cutting mechanism having a pair of opposed cutting blades, according to the present invention.

The constrained excision regions defined by cutting edges 47 and 49 are beneficial since portions of the atheroma or other material to be removed will be captured in the constrained excision regions 70 while the opposed edges cross and excise in the direction of arrows 71 in FIG. 3E. Other configurations of the cutting blades, however, will be possible. For example, opposed blades 20' and 22' (FIG. 3F) have straight, transversely aligned cutting edges 47' and 49'; respectively. Spike-like penetrating points 60' are disposed on each of the edges 47' and 49'. The penetrating points 60' will be very effective in penetrating and immobilizing tissue between the blades, but cutting may be less efficient since the material will be sheared all at once as the edges 47' and 49' meet. Note that the points 60' on the opposed edges 47' and 49' may be aligned or not, and are shown as being non-aligned.

Figure 4A:
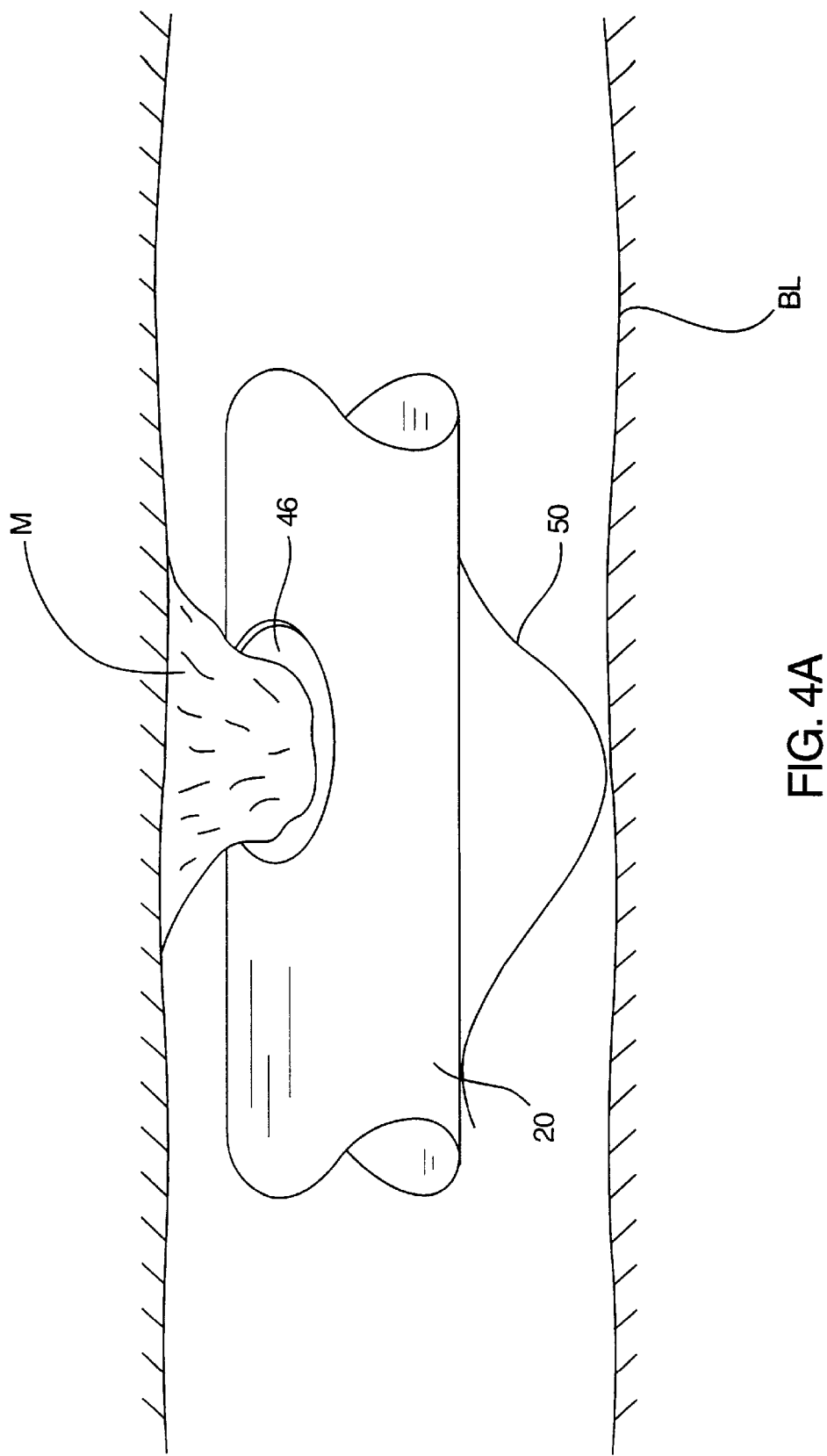
Figure 4D:
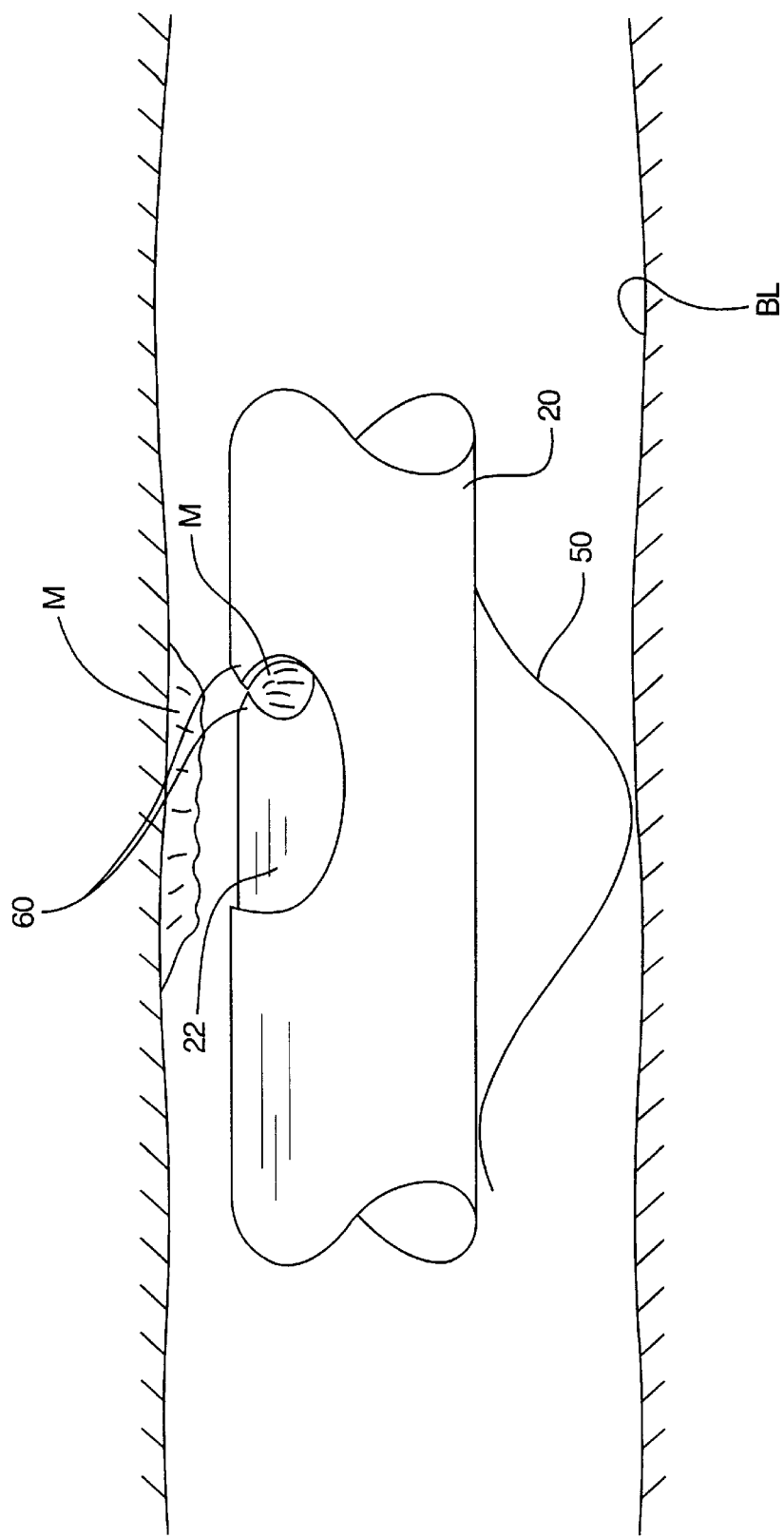

The manner in which occluding material M is removed from a body lumen BL (usually a blood vessel and more usually an artery), is illustrated in FIGS. 4A–4D. Initially, the cutting blades 20 and 22 are aligned so that aperture 46 is fully opened to receive a portion of the material M therein. The transverse urging mechanism 50 helps initially position the aperture 46 to receive a relatively large portion of the material M, as shown in FIG. 4A. After the portion of material M is initially received within the aperture 46, the inner blade 22 is proximally translated so that penetrating point 60 (one of two, three, or more of such point in this embodiment) penetrates into the material M, as shown in FIG. 4B. Note that embodiment employing only a single penetrating point may also be employed, although they are not generally preferred. The opposed penetrating point(s) 60 thus act to penetrate and capture the portion of the material M to be excised. In the absence of such penetrating points, the material would have a tendency to be extruded from the apertures as the blades 20 and 22 are closed. As the blades are further advanced (FIG. 4C), the material M continues to be excised. As the blades are closed, as shown in FIG. 4D, the material is fully excised and captured within the interior blade assembly and the catheter.

Figure 5A:
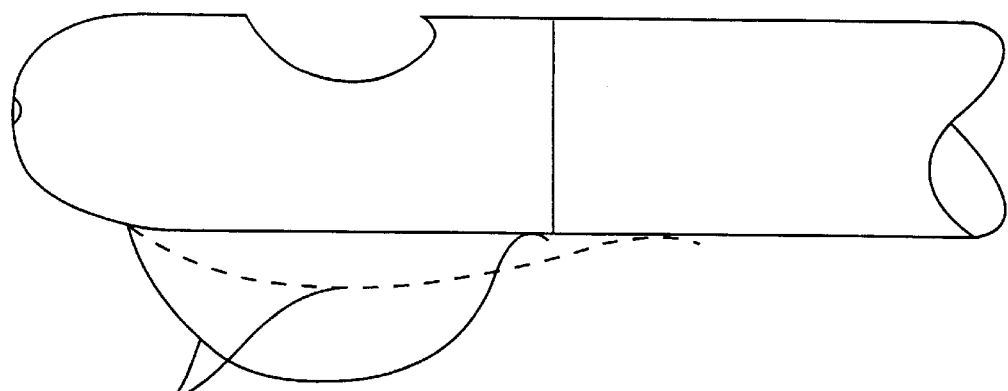
FIGS. 5A–5C illustrate alternative mechanisms for urging a distal end of an atherectomy catheter according to the present invention in a radial direction while the catheter is positioned within a body lumen.

The resilient skis 50 shown in FIG. 1 are schematically illustrated in FIG. 5A. Each of skis 50 is normally radially extended to its maximum extension, as shown in full line. When constrained by a body lumen or guiding catheter, however, the resilient ski 50 is radially compressed, as shown in broken line in FIG. 5A. The advantage of such a passive urging mechanism is that it need not be actuated and requires very little supporting mechanism. The ability to use such a passive urging mechanism is greatly facilitated by the cutting blade assembly which acts to penetrate, engage, and capture occluding material with minimum need to urge the cutter mechanism against the material.

Figure 5B:
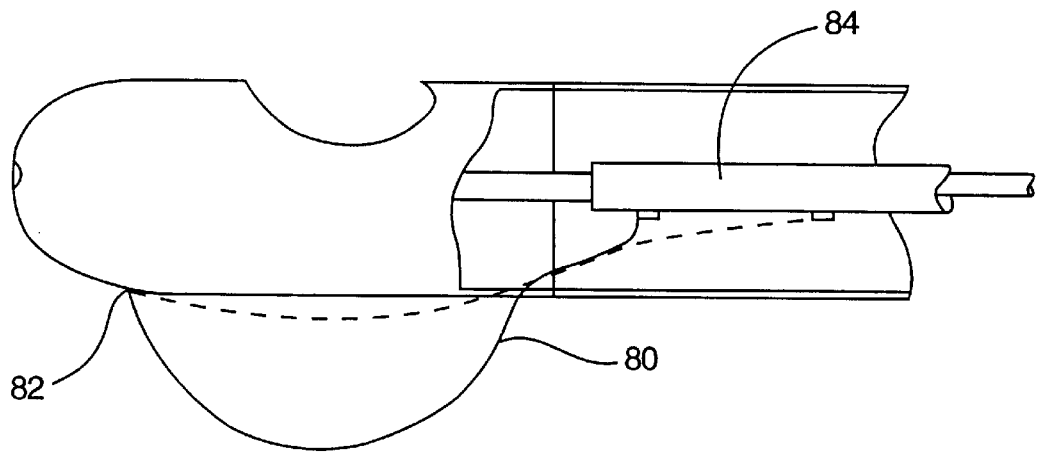

If, however, it is desired to provide positive urging, a variety of other mechanisms are possible. Although not illustrated, a balloon mechanism may be employed as disclosed in numerous prior atherectomy catheters. Other mechanical mechanisms are disclosed in FIGS. 5B and 5C. In FIG. 5B, one or more resilient skis, similar to those described previously, are fixedly attached at end 82 to the outside of a catheter body. A distal end of the element 80 is attached to an axially reciprocatable actuator sleeve 84 which extends to the proximal end of the catheter assembly (not shown). Axial advancement and retraction of the sleeve 84 thus acts to positively expand and retract the ski 80, as shown in full line and broken line respectively.

Figure 5C:
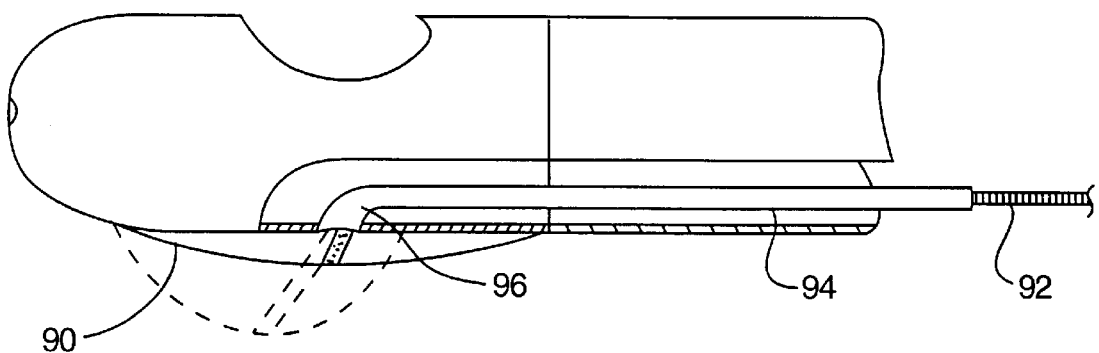

Another alternative urging mechanism is illustrated FIG. 5C. A resilient ski element or membrane 90 is secured to the outside at the side of the catheter opposite to that of a cutting aperture. A wire 92 may be advanced through a tube 94 having a deflected port 96 at its distal end. Thus, the tube 92 may extend out of the port 96 in a direction suitable for radially deploying the ski membrane element 90, as shown in broken line.

Figure 6A:
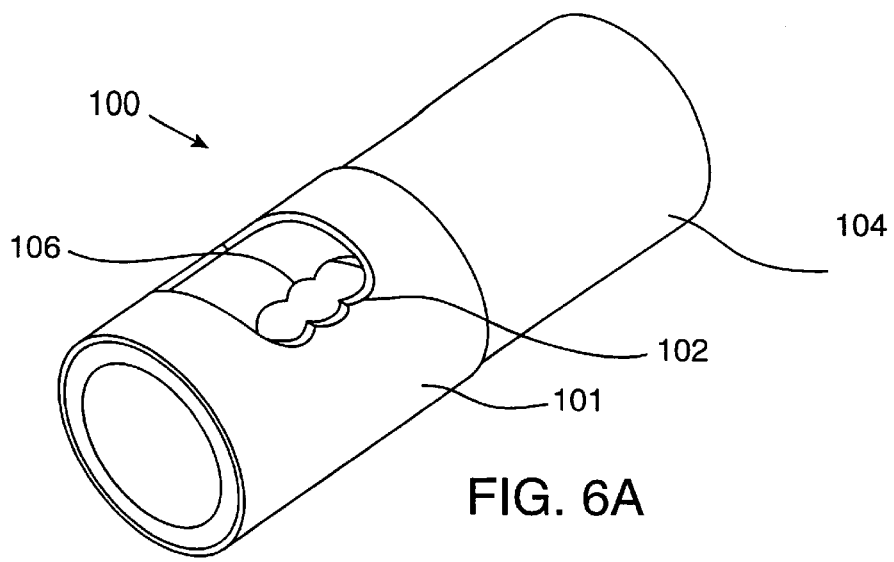
FIGS. 6A–6C illustrate an alternative cutter mechanism where axially aligned cutting edges of inner and outer cutting blades are rotationally advanced in a circumferential direction relative to each other.
Figure 6B:
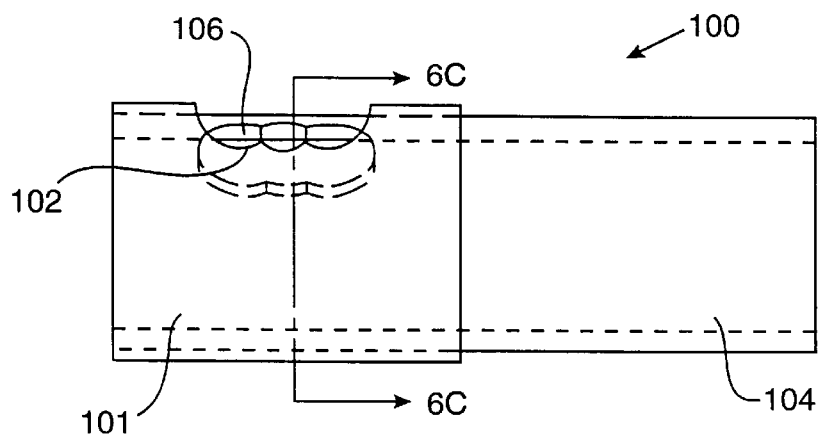
Figure 6C:
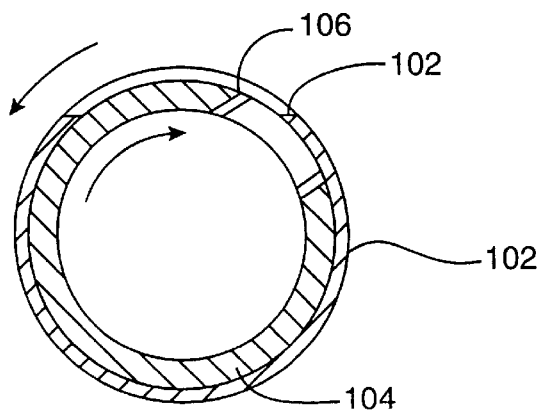
Figure 7:
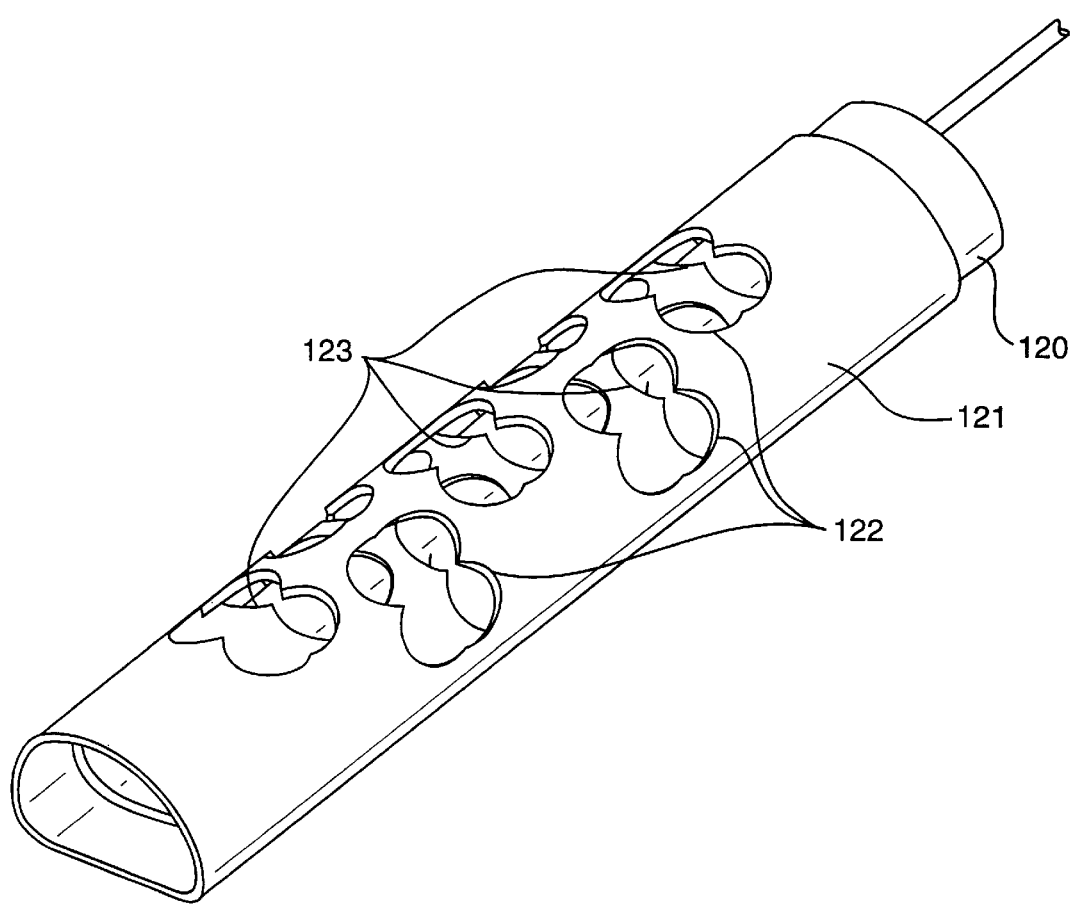
FIG. 7 illustrates an alternative embodiment of an inner cutter member having a plurality of cutting apertures.

Further alternatives to the apparatus of the present invention are illustrated in FIGS. 6 and 7. FIGS. 6A–6C illustrate a rotary cutter assembly 100 having an outer blade 101 with an axially aligned cutting edge 102, similar to those described previously. Inner cutting blade 104 also has an axially aligned cutting edge 106. Relative rotation of the inner and outer cutting blades 101 and 104 (as shown by the arrows in FIG. 6C) can thus draw the cutting edges 102 and 106 together in a manner which is otherwise fully analogous to that of the axially translatable cutting blades described previously.

FIG. 7 illustrates an inner cutting blade 120 and outer cutting blade 121, each having a plurality of cutting apertures 122 and 123 formed therein. The inner cutting blades 120 and 121 differ in several respects from the cutting blades described previously. First, they have a non-cylindrical cross-section and may thus be deployed in a blood vessel while permitting perfusion there across. The cutting apertures 122 also include penetrating points on both axial sides of the aperture. Thus, the cutting mechanism could be actuated in both proximal and distal directions. Thus, a variety of alternatives and modifications of the present invention can be achieved using designs shown in the inner cutting blade 120 of FIG. 7.

Figure 8A:
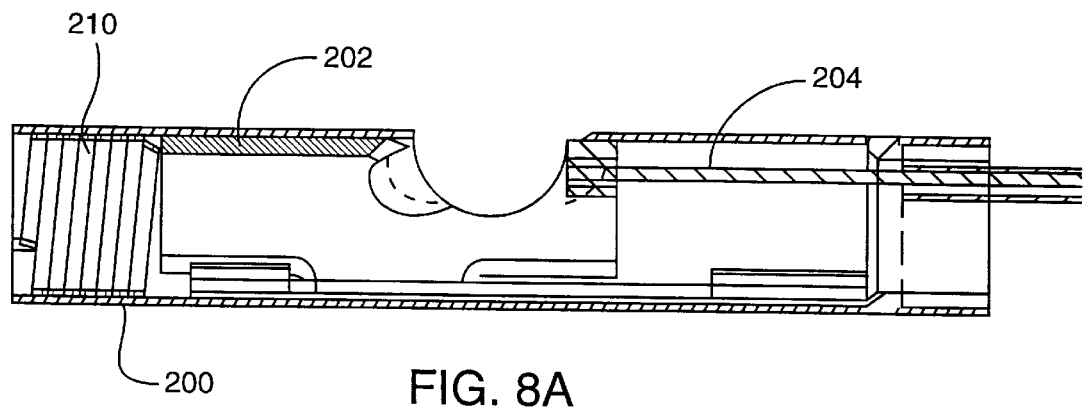
FIGS. 8A and 8B illustrate an alternative blade actuation mechanism.
Figure 8B:
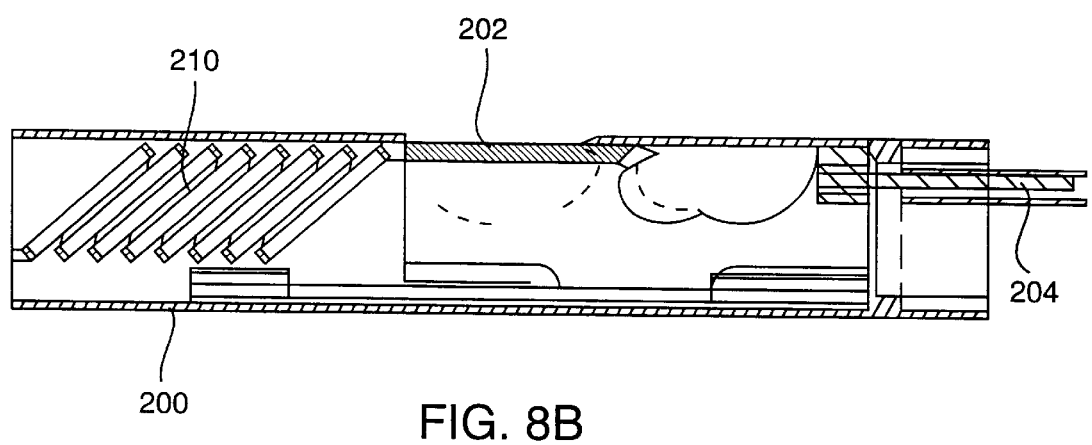

Referring now to FIGS. 8A and 8B, an alternative mechanism for the blade actuator will be described. In previous embodiments, an actuator rod or similar mechanism has been provided to directly translate a blade axially and proximally (or alternatively rotationally), depending on the direction from which the actuator is moved at the proximal end of the catheter. In some instances, however, it will be preferred to provide a spring-biased return mechanism to translate or rotate the blade in one direction. This is particularly useful with axially translated blades where "pushing" of the blade in the proximal direction requires an actuator rod having a relatively high column strength. Conversely, "pulling" of the blade in the proximal direction can be accomplished with a relatively small rod or filament since only tensile strength is required. Thus, the embodiment of FIGS. 8A and 8B includes an outer tubular blade 200 and an inner tubular blade 202. The blades 200 and 202 will be mounted to axially translate relative to each other in a manner analogous to that described for prior embodiments. The inner blade 200 is connected to an elongate actuator member 204 which will extend through the associated catheter body (not shown) to a proximal end thereof. As spring mechanism 210 is mounted on one end of the inner blade 202, preferably at its distal end as illustrated. When the inner blade 202 is advanced fully in the distal direction (as shown in FIG. 8A), the spring mechanism 210 will be relaxed. By pulling on member 204, the inner blade 202 may be retracted proximally, as illustrated in FIG. 8B. After it is fully retracted, the spring mechanism 210 will be stretched or expanded so that it applies a biasing force on the inner blade 202 in the distal direction relative to the outer blade 200. This spring mechanism 210 will be sufficiently strong, i.e. have a sufficiently high spring constant, so that the biasing force will be able to return the inner blade 202 to the distal position illustrated in FIG. 8A when force is released from the actuator member 204. Since it is the spring mechanism 210 which returns the blade 202 to the distal position, the actuator member 204 need not have significant column strength.

Figure 9:
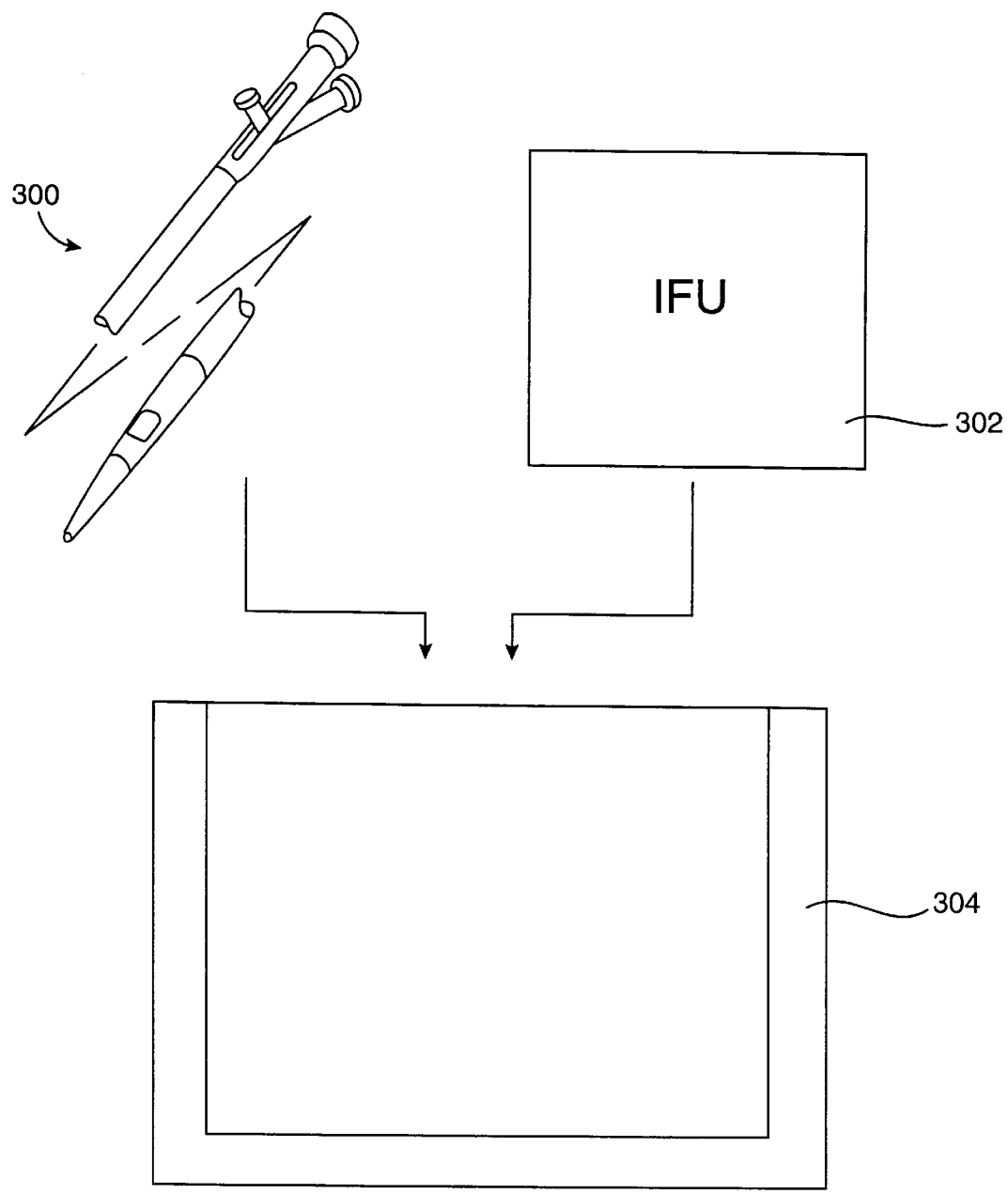
FIG. 9 illustrates a kit according to the present invention.

Referring now to FIG. 9, the present invention will further comprise kits including catheters 300, instructions for use 302, and packages 304. Catheters 300 will generally be described above, and the instruction for use (IFU) 302 will set forth any of the methods described above. Package 304 may be any conventional medical device packaging, including pouches, trays, boxes, tubes, or the like. The instructions for use 302 will usually be printed on a separate piece of paper, but may also be printed in whole or in part on a portion of the packaging 304.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A catheter comprising:
   a catheter body having a proximal end and a distal end;
   a first blade having a cutting edge and a second blade having a cutting edge disposed near the distal end of the catheter body; and
   an actuator operatively linked to the first and second blades to draw their respective cutting edges together, said blades disposed to shear tissue between the cutting edges in response to actuation by said actuator;
   wherein at least one of the cutting edges has a penetrating point disposed to penetrate and engage material to be removed as the cutting edges are passed through said material.

2. A catheter as in claim 1, wherein the cutting edges of both the first and second blades have penetrating points.

3. A catheter as in claim 2, wherein at least one of the penetrating points on the first cutting blade is aligned with one of the penetrating points on the second cutting blade so that they substantially meet as the cutting edges are drawn together.

4. A catheter as in claim 3, wherein the first cutting blade has at least two penetrating points aligned with two penetrating points on the second blade.

5. A catheter as in claim 4, wherein the first cutting blade has at least three penetrating points aligned with three penetrating points on the second cutting blade.

6. A catheter as in claim 1, wherein the actuator draws the cutting edges of the blades together in an axial direction.

7. A catheter as in claim 6, wherein the actuator comprises a rod having a distal end attached to one of the blades and a proximal end having a slider for manual advancement and retraction of the rod and blade.

8. A catheter as in claim 7, wherein the rod is radially offset in the catheter body and on the same side of a longitudinal axis of the catheter body as a cutting edge on said one of the blades.

9. A catheter as in claim 1, wherein the actuator draws the cutting edges of the blades together in a circumferential direction.

10. A catheter as in claim 1, wherein the first blade is fixedly attached to the distal end of the catheter body and the second blade moves within the first blade.

11. A catheter as in claim 10, wherein the first and second blades are arranged as coaxial tubes with side apertures which define the cutting edges.

12. A catheter as in claim 11, wherein the cutting edges are disposed transversely and the actuator translates the second blade axially relative to the first blade.

13. A catheter as in claim 11, wherein the cutting edges are disposed axially and the actuator rotates the second blade relative to the first to draw the cutting blades together circumferentially.

14. A catheter as in claim 10, wherein the second blade is spring-biased so that its cutting edge is aligned to shear closely against the cutting edge of the first blade.

15. A catheter as in claim 14, wherein the second blade is a split tube biased so that its outer surface engages against an inner surface of the first tubular blade.

16. A catheter as in claim 1, further comprising means for urging the distal end of the catheter body in a transverse direction within a body lumen.

17. A catheter as in claim 16, wherein the urging means comprises a resilient ski that projects radially outward from the catheter body.

18. A catheter as in claim 16, wherein the urging means comprises a radially extensible element and an axially translatable element for mechanically extending the element.

19. A catheter as in claim 18, wherein the radially extensible element comprises a resilient ski which is fixedly attached at its distal end to the catheter body and attached at its proximal end to the axially translatable element, wherein axial reciprocation of the translatable element causes bowing of the ski.

20. A catheter as in claim 18, wherein the radially extensible element comprises a resilient membrane and the axially translatable element is disposed to push outwardly on said membrane.

21. A catheter as in claim 1, wherein the actuator comprises a biasing element that returns the blades to an initial relative position after they have been moved by the actuator to a second position.

22. An atherectomy catheter comprising:
   a catheter body having a proximal end, a distal end, and a lumen therethrough;
   a first tubular blade having an interior and attached to the distal end of the catheter body so that said interior opens into the lumen of the catheter body;
   a second tubular blade coaxially disposed within the interior of the first tubular blade, wherein the first and second blades each have a side apertures defining transverse, opposed cutting edges and wherein each of said cutting edges has at least one penetrating point aligned with a penetrating point on the other cutting edge; and
   an actuator disposed at the proximal end of the catheter body for axially translating the second tubular blade with the first tubular blade to cause the penetrating points to penetrate material within the apertures and the cutting edges to shear material within apertures.

23. An atherectomy catheter as in claim 22, wherein the actuator comprises a rod having a distal end attached to a proximal end of the second tubular blade and a proximal end having a slider for manual advancement and retraction of the rod and second tubular blade.

24. An atherectomy catheter as in claim 23, wherein the rod is attached to a side of the second tubular blade having the side aperture therein.

25. An atherectomy catheter as in claim 22, wherein the first cutting blade has at least two penetrating points aligned with two penetrating points on the second blade.

26. An atherectomy catheter as in claim 25, wherein the first cutting blade has at least three penetrating points aligned with three penetrating points on the second cutting blade.

27. An atherectomy catheter as in claim 22, wherein the inner blade is spring-biased so that its cutting edge is aligned to shear closely against the cutting edge of the first blade.

28. An atherectomy catheter as in claim 27, wherein the inner blade is a split tube biased so that its outer surface engages against an inner surface of the outer tubular blade.

29. An atherectomy catheter as in claim 22, further comprising means for urging the distal end of the catheter body in a transverse direction within a body lumen.

30. An atherectomy catheter as in claim 29, wherein the urging means comprises a resilient ski that projects radially outward from the catheter body.

31. An atherectomy catheter as in claim 29, wherein the urging means comprises a radially extensible element and an axially translatable element for mechanically extending the radially extensible element.

32. An atherectomy catheter as in claim 31, wherein the radially extensible element comprises a resilient ski which is fixedly attached at its distal end to the catheter body and attached at its proximal end to the axially translatable element, wherein axial reciprocation of the translatable element causes bowing of the ski.

33. An atherectomy catheter as in claim 31, wherein the radially extensible element comprises a resilient membrane and the axially translatable element is disposed to push outwardly on said membrane.

34. An atherectomy catheter as in claim 22, wherein the actuator comprises a biasing element that returns the blades to an initial relative position after they have been moved by the actuator to a second position.

35. A method for excising occlusive material from within a body lumen, said method comprising:

disposing a first blade within the body lumen so that a cutting edge of said blade is on one side of a portion of said material;

disposing a second blade within the body lumen so that a cutting edge of said second blade is on another side of said portion of said material wherein at least one of said blades has a penetrating point on its cutting edge; and drawing the blades together to first penetrate the penetrating point into said material and thereafter to shear the portion between the cutting edges.

36. A method as in claim 35, wherein the disposing steps comprises intraluminally advancing the blades on a catheter.

37. A method as in claim 36, wherein the body lumen is blood vessel and the occlusive material is selected from the group consisting of clot, thrombus, atheroma, and plaque.

38. A method as in claim 35, wherein the drawing step excises a volume of material in the range from 0.1 mg to 5 mg.

39. A method as in claim 35, wherein the cutting edges of both the first and second blades have penetrating points.

40. A method as in claim 39, wherein at least one of the penetration points on the first cutting blade is aligned with one of the penetrating points on the second cutting blade so that they substantially meet as the cutting edges are drawn together.

41. A method as in claim 40, wherein the first cutting blade has at least two penetrating points aligned with two penetrating points on the second blade.

42. A method as in claim 41, wherein the first cutting blade has at least three penetrating points aligned with three penetrating points on the second cutting blade.

43. A method as in claim 35, wherein the drawing step comprises translating the blades relative to each other in a direction aligned with an axis of the body lumen.

44. A method as in claim 35, wherein the drawing step comprises rotating the blades in a circumferential direction relative to each other with respect to an axis of the body lumen.

45. A method as in claim 35, further comprising removing excised material from the body lumen.

46. A method as in claim 35, wherein the drawing step is repeated a plurality of times to penetrate and shear a plurality of occlusive material portions.

47. A method as in claim 35, further comprising radially engaging the blades against a target site on the lumenal wall.

48. A method as in claim 47, wherein the radially engaging step comprises urging the blades with at least one radially disposed resilient ski.

49. A catheter comprising:

a catheter body having a proximal end and a distal end;

a first blade having a cutting edge and a second blade having a cutting edge disposed near the distal end of the catheter body; and an actuator operatively linked to the first and second blades to draw their respective cutting edges together;

wherein both the first and second blades have penetrating points disposed to penetrate and engage material to be removed as the cutting edges are passed through said material.

50. A catheter as in claim 49, wherein at least one of the penetrating points on the first cutting blade is aligned with one of the penetrating points on the second cutting blade so that they substantially meet as the cutting edges are drawn together.

51. A catheter as in claim 50, wherein the first cutting blade has at least two penetrating points aligned with two penetrating points on the second blade.

52. A catheter as in claim 51, wherein the first cutting blade has at least three penetrating points aligned with three penetrating points on the second cutting blade.

53. A catheter comprising:

a catheter body having a proximal end and a distal end;

a first blade having a cutting edge and a second blade having a cutting edge disposed near the distal end of the catheter body; and an actuator operatively linked to the first and second blades to draw their respective cutting edges together in an axial direction, said actuator comprising a rod radially offset in the catheter body and having a distal end attached to one of the blades, said rod axially aligned with a cutting edge on said blade, and a proximal end having a slider for manual advancement and retraction of the rod and said one of the blades;

wherein at least one of the cutting edges has a penetrating point disposed to penetrate and engage material to be removed as the at least one cutting edge is passed through said material.

54. A catheter comprising:

a catheter body having a proximal end and a distal end;

a first blade having a cutting edge and a second blade having a cutting edge disposed near the distal end of the catheter body; and an actuator operatively linked to the first and second blades to draw their respective cutting edges together, said blades mounted to shear tissue between the cutting edges;

wherein at least one of the cutting edges has a penetrating point disposed to penetrate and engage material to be removed as the at least one cutting edge is passed through said material;

wherein the first and second blades are arranged as coaxial tubes with side apertures which define the cutting edges, said first blade is fixedly attached to the distal end of the catheter body and the second blade moves within the first blade.

55. A catheter as in claim 54, wherein the cutting edges are disposed transversely and the actuator translates the second blade axially relative to the first blade.

56. A catheter as in claim 54, wherein the cutting edges as disposed axially and the actuator rotates the second blade relative to the first to draw the cutting blades together circumferentially.

57. A catheter comprising:

a catheter body having a proximal end and a distal end;

a first blade having a cutting edge and a second blade having a cutting edge disposed near the distal end of the catheter body, wherein the second blade is spring-biased so that its cutting edge is aligned to shear closely against the cutting edge of the first blade; and an actuator operatively linked to the first and second blades to draw their respective cutting edges together;

wherein at least one of the cutting edges has a penetrating point disposed to penetrate and engage material to be removed as the at least one cutting edge is passed through said material.

58. A catheter as in claim 57, wherein the second blade is a split tube biased so that its outer surface engages against an inner surface of the first blade.

59. A catheter comprising:

a catheter body having a proximal end and a distal end;

a first blade having a cutting edge and a second blade having a cutting edge disposed near the distal end of the catheter body;

an actuator operatively linked to the first and second blades to draw their respective cutting edges together;

wherein at least one of the cutting edges has a penetrating point disposed to penetrate and engage material to be removed as the at least one cutting edge is passed through said material; and means for urging the distal end of the catheter body in a transverse direction within a body lumen, wherein the urging means comprises a radially extensible element and an axially translatable element for mechanically extending the radially extensible element.

60. A catheter as in claim 59, wherein the radially extensible element comprises a resilient ski which is fixedly attached at its distal end to the catheter body and attached at its proximal end to the axially translatable element, wherein axial reciprocation of the translatable element causes bowing of the ski.

61. A catheter as in claim 59, wherein the radially extensible element comprises a resilient membrane and the axially translatable element is disposed to push outwardly on said membrane.

62. A method for excising occlusive material from within a body lumen, said method comprising:

disposing a first blade within the body lumen so that a cutting edge of said blade is on one side of a portion of said material;

disposing a second blade within the body lumen so that a cutting edge of said second blade is on another side of said portion of said material wherein at least one of said blades has at least one penetrating point thereon; and drawing the blades together to first penetrate the penetrating point into said material and thereafter to shear the portion with the cutting edges, wherein the cutting edges of both the first and second blades have penetrating points.

63. A method as in claim 62, wherein at least one of the penetrating points on the first cutting blade is aligned with one of the penetrating points on the second cutting blade so that they substantially meet as the cutting edges are drawn together.

64. A method as in claim 63, wherein the first cutting blade has at least two penetrating points aligned with two penetrating points on the second blade.

65. A method as in claim 64, wherein the first cutting blade has at least three penetrating points aligned with three penetrating points on the second cutting blade.

66. A method for excising occlusive material from within a body lumen, said method comprising:

disposing a first blade within the body lumen so that a cutting edge of said blade is on one side of a portion of said material;

disposing a second blade within the body lumen so that a cutting edge of said second blade is on another side of said portion of said material wherein at least one of said blades has a penetrating point thereon; and drawing the blades together to first penetrate the penetrating point into said material and thereafter to shear the portion with the cutting edges;

radially engaging the blades against a target site on the luminal wall, wherein radially engaging the blades comprises urging the blades with at least one radially disposed resilient ski.

* * * * *